US00PP09274P

United States Patent [19]

Olesen et al.

[11] Patent Number: Plant 9,274

[45] Date of Patent: Sep. 5, 1995

[54] HYBRID TEA ROSE PLANT NAMED 'POULART'

[75] Inventors: Pernille Olesen; Mogens N. Olessen, both of Fredensborg, Denmark

[73] Assignee: DeVor Nurseries, Inc., Watsonville, Calif.

[21] Appl. No.: 310,713

[22] Filed: Sep. 21, 1994

[51] Int. Cl.[6] ..... A01H 5/00

[52] U.S. Cl. ..... Plt./14

[58] Field of Search ..... Plt. 14, 15, 23, 24

*Primary Examiner*—Howard J. Locker

*Attorney, Agent, or Firm*—Christie, Parker & Hale

[57] ABSTRACT

A new variety of Hybrid Tea rose plant producing white flowers.

1 Drawing Sheet

SUMMARY OF THE INVENTION

The present invention relates to a new and distinct variety of rose plant of the Hybrid Tea rose class which was originated by my crossing as seed parents two unnamed, unpatented, proprietary seedlings of our creation. The varietal denomination of this new rose is 'Poulari'.

Among the novel characteristics possessed by this new variety which distinguishes it from its parents are its attractive white flowers produced on a plant with shiny foliage and which open well in both hot and cool climates.

Asexual reproduction by budding of the new variety as performed in Watsonville, Calif., shows that the foregoing and other distinguishing characteristics come true to form and are established and transmitted through succeeding propagations.

BRIEF DESCRIPTION OF ILLUSTRATION

The accompanying illustration shows typical specimens of the flowers and vegetative growth of the new variety depicted in color as nearly true as it is reasonably possible to make the same in a color illustration of this character. Phenotypic expression, including colors, may vary depending upon growing conditions, such as climate, soil, and cultivation conditions.

DESCRIPTION OF THE NEW VARIETY

The following is a detailed description of my new variety, with color terminology in accordance with The Royal Horticultural Society Color Chart (RHSCC). The terminology used in color description herein refers to plate numbers in the aforementioned color chart. Where general terms such as average, normal, ordinary, medium, etc. are used, the characteristics so described are not considered distinguishing.

Parentage: Seedling.

*Seed parent.*—Unnamed seedling.

*Pollen parent.*—Unnamed seedling.

Class: Hybrid tea.

The following information is from observations made of specimens grown outdoors in Watsonville, Calif. in the month of May.

FLOWER

Blooming habit: Recurrent.

A. Bud:

(1) *Size.*—Large.

(2) *Form.*—Pointed, slightly tapering.

(3) *Color.*—As sepals divide, bud color is near 150C.

(4) *Sepals.*—Longer than bud, slightly foliage. Color: Near 146B.

(5) *Peduncle.*—Length: About 18 to 20 cm. Aspect: Smooth. Strength: Sturdy, erect. Color: Near 144B.

(6) *Bracts.*—Some. Color — near 146A. Form — broadly elliptical with acute tip. Location in relation to flower — about 4 to 10 cm below bud.

B. Bloom:

(1) *Size.*—About 12 to 14 cm.

(2) *Borne.*—Sprays of up to 7 to 15 blooms.

(3) *Form.*—Imbricated, becoming informal at maturity, outer petals relflex, inner petals roll under. p2 (4) *Petalage.*—Number of petals under condition — about 55 to 75.

(5) *Color.*—$\frac{1}{3}$ to $\frac{1}{2}$ open: Outer petals — top surface near 155B with 157B adjacent bottom. Undersurface near 155C with near 155A adjacent bottom. Inner petals — top surface 155B with 155A adjacent bottom. Undersurface 155D with 157A adjacent bottom. Base of petals (point of attachment) 145C. General tonality from a distance — white. Fully open bloom: Outer petals — Top surface 155D with near 157D adjacent bottom. Undersurface 155D Inner petals — Top surface 155D with near 157D adjacent bottom. Undersurface 155D. Base of petals (point of attachment) 160D. General tonality from a distance — white. Color Change: Color gets whiter as bloom ages. Petal top surface — white. Petal undersurface — white. General tonality at a distance — white.

C. Petals:

(1) *Texture.*—Thick.

(2) *Appearance.*—Matte on both sides.

(3) *Form.*—Orbicular with ruffles.

(4) *Arrangement.*—Imbricated.

(5) *Petaloids in center.*—Few.

(6) *Petals drop off cleanly.*

(7) *Fragrance.*—Mild fruity fragrance.

(8) *Lasting quality.*—Long lasting on plant.

REPRODUCTIVE ORGANS

A. Stamens, filaments and anthers:

*Arrangement.*—Irregularly arranged around styles.

*Stamens.*—Color — near 150D.

*Filaments.*—Color near 145C.

*Anthers.*—Color near 22B.

*Pollen.*—Color near 22B.

B. Styles: Bunched, even.

*Stigma.*—Color —near 160A.

PLANT

A. Form: Upright.

B. Growth: Very vigorous.

*Height attained (first season).*—About 60 to 100 cm.

C. Foliage: Compound 3 to 5 leaflets.

(1) *Size.*—Large.

(2) *Quantity.*—Abundant.

(3) *Color.*—New foliage: Upper side near 187A. Underside near 187A. Old foliage: Upper side near 147A. Underside — near 147B.

(4) *Shape.*—Oval.

(5) *Texture.*—Upper side is glossy, slightly leathery and underside is dull and very slightly leathery.

(6) *Edge.*—Serrated.

(7) *Serration.*—Denticulate.

(8) *Petiole color.*—Top surface — near 166A with tinges of near 147B on sides. Underside near 146C.

(9) *Stipules.*—Adnate, medium, slightly bearded.

(10) *Auricle.*—Slender with small glands at top.

(11) *Rachis.*—Small prickles underneath.

(12) *Resistance to disease.*—Very resistant to mildew, rust and blackspot.

D. Wood:

(1) *New wood.*—Color —near 187B with near 144B throughout. Bark — smooth.

(2) *Old wood.*—Color —near 146B. Bark — smooth.

(3) *Flower stem length from last cutting.*—About 35 cm.

E. Thorns:

*Quantity (main stalk).*—Ordinary, young thorns near 187B.

*On laterals from stalk.*—Few.

*Form.*—Winged shaped and dilated.

*Length.*—Medium.

*Position.*—Irregular.

*Prickles.*—None.

F. Winter hardiness: Winter hardy in coastal California climate.

I claim:

1. A new and distinct variety of rose plant of the Hybrid Tea rose class, substantially as shown and described.

* * * * *

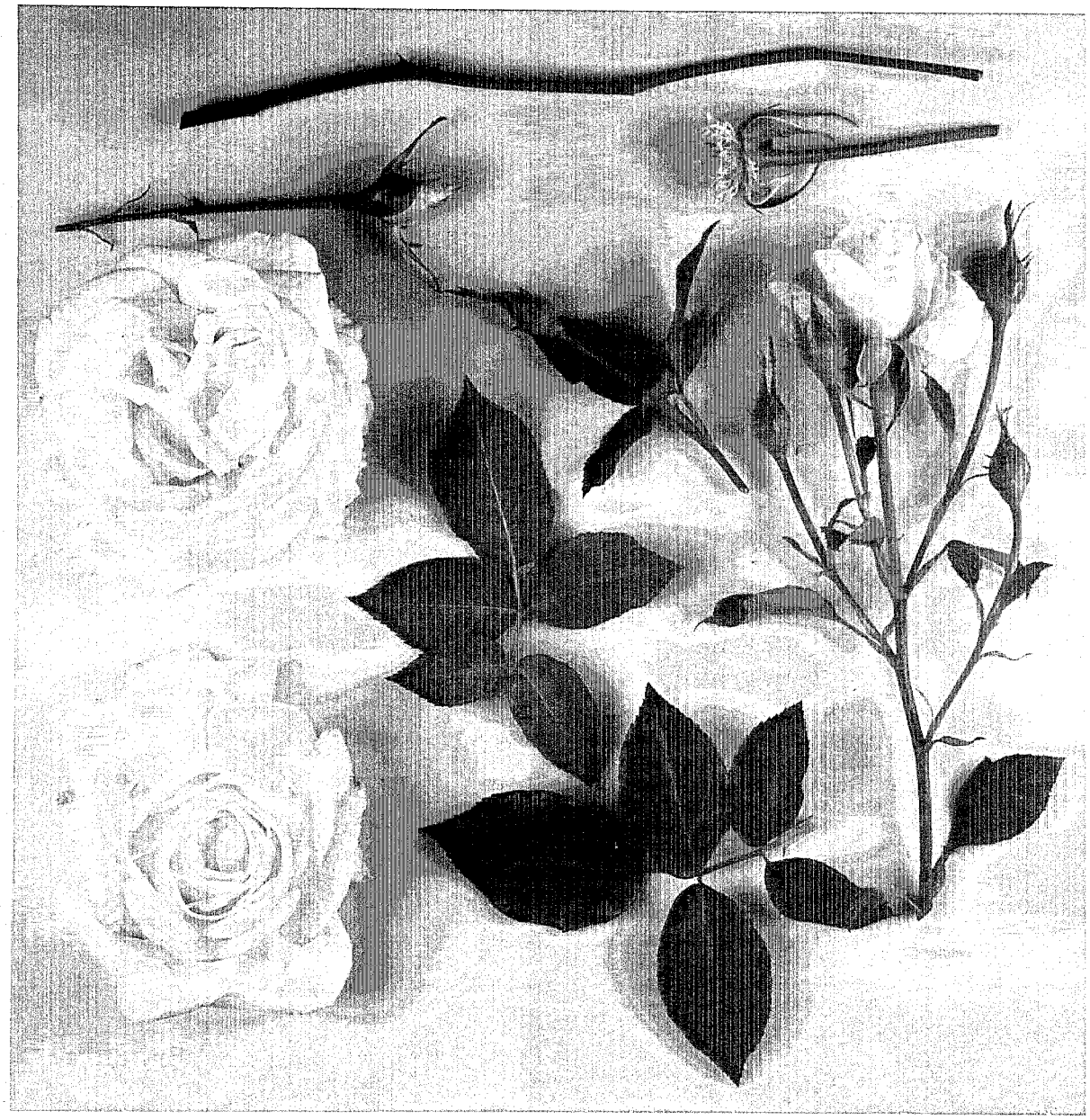

UNITED STATES PATENT AND TRADEMARK OFFICE

CERTIFICATE OF CORRECTION

PATENT NO. : Plant 9,274

DATED : September 5, 1995

INVENTOR(S) : Pernille Olesen; Mogens N. Olesen

It is certified that error appears in the above-indentified patent and that said Letters Patent is hereby corrected as shown below:

Title page:
Item 54, in the title, change "'POULART'" to
-- 'POULARI' --.

Item 75, Inventors, change "Mogens N. Olessen" to
-- Mogens N. Olesen --.

Column 2, line 9, change "foliage" to -- foliated --.

Column 2, lines 23,24, change to read as follows:
-- der.
(4) *Petalage*.– Number of petals under normal conditions – about 55 to 75. --.

Column 2, line 47, change "(6) *Petals drop off cleanly*." to -- (6) *Persistance*.– *Petals drop off cleanly*. --.

Signed and Sealed this

Thirtieth Day of July, 1996

*Attest:*

Bruce Lehman

BRUCE LEHMAN

*Attesting Officer*

*Commissioner of Patents and Trademarks*